United States Patent [19]
Claasen

[11] 4,023,675
[45] May 17, 1977

[54] PACKING FOR IMPRESSION MATERIAL FOR DENTAL USE

[76] Inventor: Antonius Bernardus Claasen, Sperwerlaan 4, Leende, Netherlands

[22] Filed: Jan. 23, 1976

[21] Appl. No.: 651,812

[30] Foreign Application Priority Data
Jan. 29, 1975 Netherlands .................. 7501034
June 19, 1975 Netherlands .................. 7507318

[52] U.S. Cl. .......................... 206/219; 206/221; 259/18
[51] Int. Cl.² .................................. B65D 25/08
[58] Field of Search ............ 206/219, 221; 259/18

[56] References Cited
UNITED STATES PATENTS
3,462,070  8/1969  Corella .................. 206/221
3,741,381  6/1973  Thompson et al. ........ 206/221

*Primary Examiner*—George T. Hall
*Attorney, Agent, or Firm*—O'Brien & Marks

[57] ABSTRACT

Packing for impression material for dental use, comprising a container of flexible material divided into two compartments, wherein for the separation of the compartments the walls thereof are locally compressed by a clamping member, wherein the clamping member is adapted to receive the compressed container wall portions according to a labyrinth path.

16 Claims, 10 Drawing Figures

PACKING FOR IMPRESSION MATERIAL FOR DENTAL USE

The present invention relates to a packing for impression material for dental use, comprising a container of flexible material divided into two compartments, and a clamping member for separating the compartments by locally compressing the walls thereof.

In a prior art packing also known for separately receiving a liquid and powdered phase, the clamping member comprises a rigid, circular pin and a resilient clamp fitted around it for clamping the container wall portions. Such a clamp has the drawback that it can easily be displaced when the compartments are filled.

The object of the invention is to remove this drawback.

To this end the clamping member according to the invention is characterized in that it is disposed to receive the compressed container wall portions according to a labyrinth path. The labyrinth path can thereby comprise at least two oppositely oriented, successive loop-shaped path sections.

According to an embodiment of the invention, the clamping member can have a passage opening for the container wall portions in its centre, while on both sides of the passage opening there are provided opposed folding portions for receiving folded-back container portions under clamping action. The clamping member can consist of sheet-like, flexible material. Such a clamping member has the advantage of being releasable with a single pull at the opposed container ends without parts thereof flying about. Another advantage is that the clamping member consists of a single piece.

According to another embodiment of the invention, in which also the main elements are applied, the clamping member is formed by two parts lockable with respect to each other and forming each separately or jointly a substantially prismatic body, between which parts the container wall is clampingly received. Such a clamping member had the advantage that it can be placed on one of the container's ends after release from the container, during which the container can be stressed again by rolling it up by means of the clamping member and subsequently shaken. After shaking, the container can be squeezed out by means of the clamping member after an outlet has been made at the end opposite the clamping member.

To promote easy rolling of the clamping member, at least one of the two lockable parts can be provided with a handle-like extension. This extension can have the form of a spatula, which after having squeezed out the mass from the container can be used for other purposes, for instance distributing the impression material in the mould or impression tray.

Furthermore the clamping member can include two clamping halves interconnected at one end hingeably and at the other end by means of a locking member. The facing surfaces of the clamping halves can be provided with longitudinally extending, engaging, conical ribs and grooves. To ensure proper sealing, also in case of slight deflection of the clamping halves under the influence of the container wall received therebetween, at least one rib or one groove is arranged in the centre of said surfaces.

The clamping member can also comprise two substantially concentric parts which can rotate relative to one another and include slots for passing the container wall. To lock the rotatable parts with respect to one another, the outer wall of the inner portion and the inner wall of the outer portion can be provided with one or more raised parts and recesses which engage snappingly.

The present invention also relates to a packing suitable for being placed in a shaker or vibrator.

The invention will now be described in more detail with reference to the drawings showing several embodiments of the packing by way of example. In the drawings.

Figure 4:
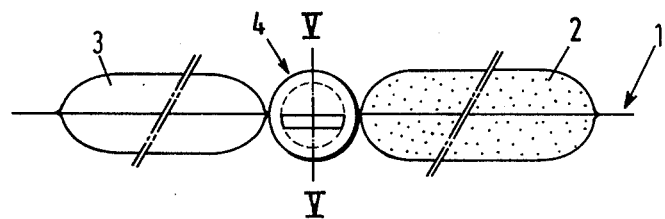
FIG. 4 is a longitudinal sectional view of a second embodiment of the packing according to the invention.
Figure 5:
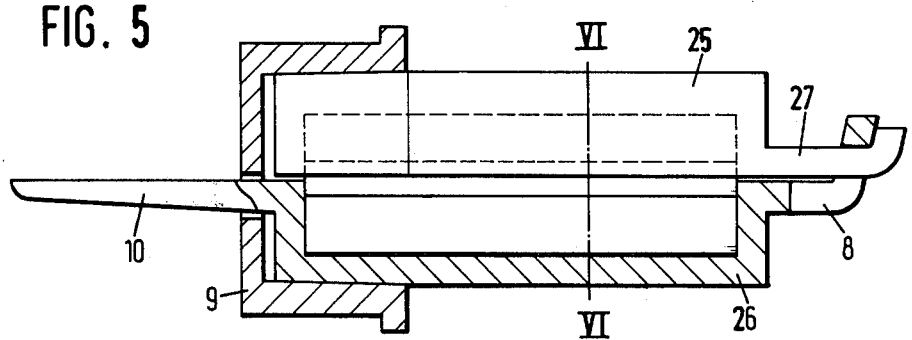
Figure 6:
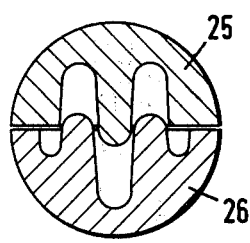
Figure 7:
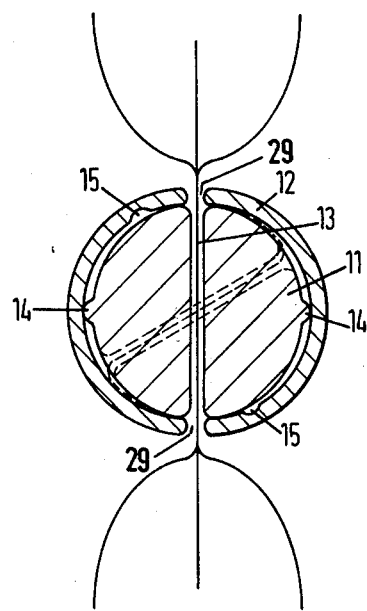
Figure 8:
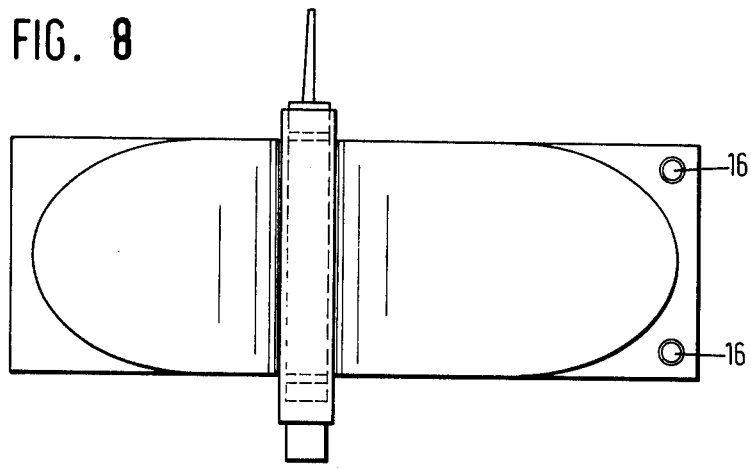
Figure 9:
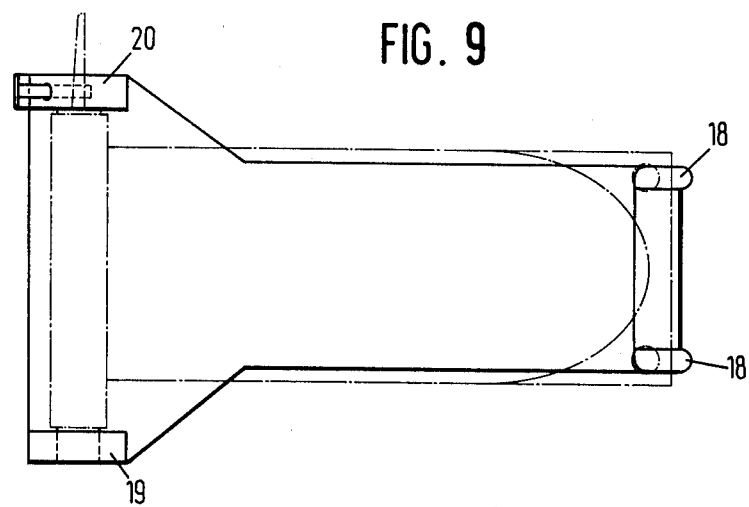
Figure 10:
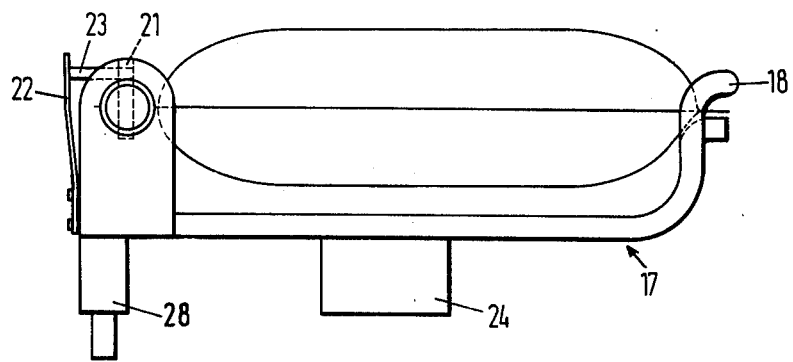

FIG. 5 enlarges a sectional view taken along line V—V in FIG. 4;

FIG. 6 is a sectional view taken along line VI—VI in FIG. 5;

FIG. 7 is a cross-sectional view of a third embodiment of the clamping member according to the invention;

FIG. 8 is an enlarged top view of the packing shown in FIG. 4, but using the clamping member shown in FIG. 7;

FIG. 9 is a top view of the packing shown in FIG. 4 received in an attachment suited for being placed in a vibrator; and FIG. 10 is a side elevational view of the apparatus shown in FIG. 9.

Figure 1:
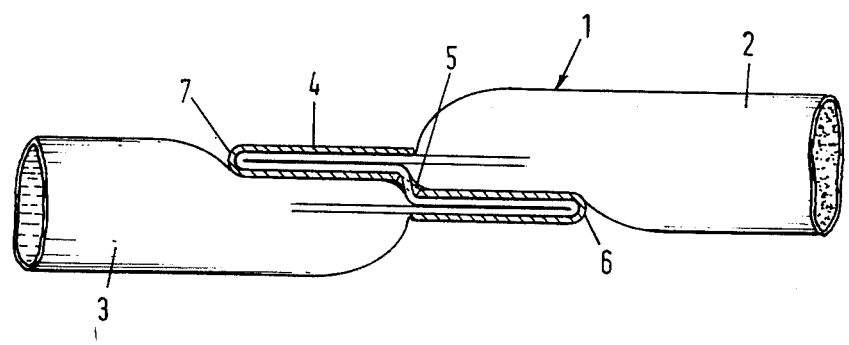
FIG. 1 is a side elevational view of part of a packing with a closed clamping member.
Figure 2:
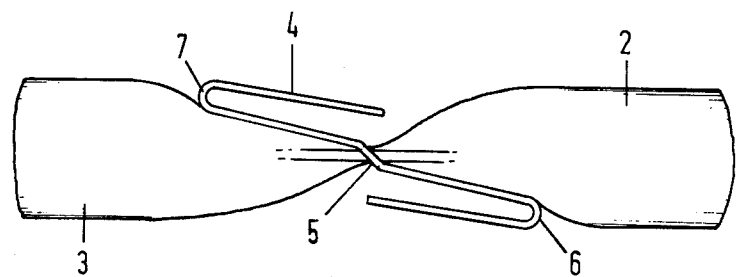
FIG. 2 is a view in accordance with FIG. 1 with an open clamping member.
Figure 3:
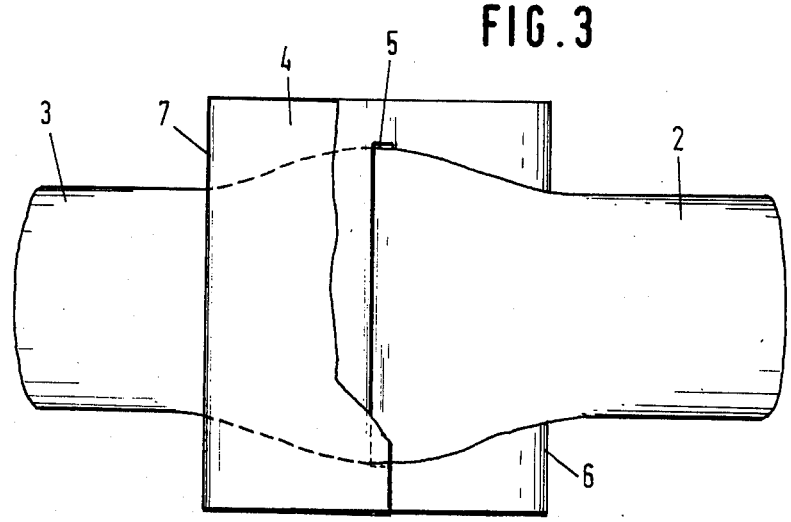
FIG. 3 shows on a reduced scale a top view of the packing according to FIG. 1.

As can be seen in FIGS. 1–3, container 1 made of a flexible plastics tube, for example polyvinylchloride (PVC), is divided into two compartments 2 and 3 by a clamping member 4. Compartments 2 and 3 can be closed after filling at their end facing away from the clamping member 4 by subjecting them to a sealing treatment.

Clamping member 4 consists essentially of a sheet-like flexible material having centrally arranged therein a slot-like opening 5 for receiving the container. Further to the apertured part 5, the sheet-like material is bent in opposite directions on both sides, while the remaining parts have opposed folding lines 6 and 7, respectively, each adapted to receive folded-back container parts with clamping action (FIG. 1). The material of the clamping member, its thickness and the clamping action are selected such that the folded-back container parts are released by exerting a pulling force by hand on the container end portions (FIG. 2). The clamping member can then easily be removed by sliding along the container.

The embodiments shown in FIGS. 4–10 also show a packing for impression material for dental use, including a tubular container 1 of synthetic material, for example PVC, the ends of which are closed by sealing. The container is divided into two compartments 2 and 3 by a clamping member 4. These compartments may be filled, for example, with preserved, sterile water or powdered impression material.

As can be seen in FIGS. 5 and 6, clamping member 4 includes two parts 25 and 26, of which part 25 is provided with a hook-shaped projection 27 and the other part 26 with a hook-shaped portion 8 including an eye, which projections can cooperate hingeably. The other ends of parts 25 and 26 are kept together by an annular gripping piece 9, the inner wall of which is slightly conical in order to ensure proper clamping.

To ensure proper sealing between the compartments, parts 25 and 26 (as shown in FIG. 6) are provided with longitudinally extending engaging conical ribs and grooves at the facing surfaces.

Before use of the impression material the clamping member is removed, so that the powdered material and the water can come into contact with one another. To obtain proper admixture, the clamping member is subsequently put onto one of the ends of the packing and rolled up like a tube. In this condition the packing is placed in an attachment, which is adapted to cooperate with a shaker or vibrator, as will be explained later on with reference to FIGS. 9 and 10.

After removal from the shaker, the end opposite the clamping member is provided with an outlet opening, after which the impression material is squeezed out by further rolling up the clamping member and is put into a so called impression tray.

To facilitate said rolling, either one of parts 25 or 26, in the drawings part 26, has a handle-like extension 10. By constructing this extension in the form of a spatula, it can be used for equally distributing the impression material over the impression tray after said impression tray is filled and the container fully or almost fully emptied.

In the embodiment shown in FIG. 7 the clamping member includes two substantially concentric parts 11 and 12 which are rotatable relative to one another. The inner part 11 includes a slot 13 and the outer part 12 includes slots 29. Slots 13 and 29 are disposed to receive, container 1. By rotation of part 11 relative to part 12 the container wall is clamped therebetween in liquid-tight fashion. In order to lock parts 11 and 12 in this clamping position relative to one another they are provided with raised portions 14 and recesses 15, respectively, which cooperate snappingly.

The clamping member shown in FIG. 7, also used in the packing shown in FIG. 8, need not first be removed from the packing before use of the impression material and after which it can be put onto one of the ends. Instead the clamping member may be displaced to one of the ends of the packing simply by sliding by rotation of parts 11 and 12 back into the position shown in FIG. 7 in fully drawn lines.

In order to arrange the packing easily on the attachment 17 shown in FIGS. 9 and 10, said packing is provided with apertures (16) at the sealed portions (FIG. 8), which openings can cooperate with hooks 18 of the attachment. At the end opposite the hooks, the attachment is provided with two supports 19 and 20, adapted to receive the clamping member. The support 19 is adapted to receive the cylindrical end of the clamping member, whereas support 20 is adapted to receive the spatula-like extension 10. For the latter purpose, a slot 21 is provided in support 20, the open end of which slot is closed by a pin 23 attached to a leaf spring 22.

The attachment 17 is furthermore provided on the lower sides with two projecting parts 24 and 28, adapted to cooperate with a known vibrator (not shown).

It will be clear that the invention is not limited to the embodiments described above and shown in the drawings but that a great number of variants are possible without departing from the scope of the present invention.

I claim:

1. A packing container for dental impression material which container comprises in combination, a container portion having walls formed of flexible material and having a restricted area defining two compartments, a clamping means having a passage disposed to encircle the restricted area and having separate means oppositely disposed relative a perpendicular plane through said passage for convolutely clamping the wall portions of the container.

2. The packing container of claim 1 wherein the said separate means comprises at least two, oppositely oriented, successive, loop-shaped path sections.

3. The packing container of claim 1 wherein the clamping means has the passage for the container wall at its center, and the oppositely directed folding means projecting from the passage for receiving folded-back container portions under clamping action.

4. The packing container of claim 3 wherein the clamping means is formed of sheet-like material.

5. The packing container of claim 3 wherein the clamping means is formed of flexible material.

6. The packing container of claim 1 wherein the clamping means has two parts which are lockable with respect to one another and which form each individually or jointly a substantially prismatic body between which parts the restricted area of the container is received clampingly.

7. The packing container of claim 6 wherein at least one of the two mutually lockable parts is provided with a handle-like extension.

8. The packing container of claim 7 wherein the extension is a spatula.

9. The packing container of claim 6 wherein the clamping means comprises two clamping halves which interconnect at one end by a hinge and at the other end by a locking member.

10. The packing container of claim 9 wherein facing surfaces of the clamping halves include longitudinally extending, engaging ribs and grooves, said ribs and grooves being conical in configuration.

11. The packing container of claim 10 wherein at least one rib and one corresponding groove are disposed at the center of the facing surfaces.

12. The packing container of claim 9 wherein the locking member is formed by an annular gripping piece, the inner wall of which is slightly conical.

13. The packing container of claim 6 wherein the clampine member comprises two mutually rotatable, substantially concentric elements having slots for receiving the container walls.

14. The packing container of claim 13 wherein the outer wall of the inner portion and the inner wall of the outer portion are provided with one or more raised portions and mating recesses which cooperate snappingly.

15. The packing container of claim 1 having means adapted to be placed in a shaker.

16. The packing container of claim 15 wherein the said means include apertures disposed along an edge portion of the packing container.

* * * * *